United States Patent [19]
Satake et al.

[11] Patent Number: 5,869,499
[45] Date of Patent: Feb. 9, 1999

[54] BENZYLOXYQUINUCLIDINES AS SUBSTANCE P ANTAGONISTS

[75] Inventors: Kunio Satake, Handa; Hiroaki Wakabayashi, Kariya, both of Japan

[73] Assignee: Pfizer Inc, New York, N.Y.

[21] Appl. No.: 637,682

[22] PCT Filed: Jul. 5, 1994

[86] PCT No.: PCT/JP94/01092

§ 371 Date: Mar. 3, 1996

§ 102(e) Date: Mar. 3, 1996

[87] PCT Pub. No.: WO95/02595

PCT Pub. Date: Jan. 26, 1995

[30] Foreign Application Priority Data

Jul. 15, 1993 [JP] Japan ................... 5-175609

[51] Int. Cl.[6] .............. A61K 31/44; A61K 31/435; C07D 453/02; C07D 401/00

[52] U.S. Cl. .............. 514/305; 514/63; 514/228.2; 514/235.2; 514/255; 544/61; 544/69; 544/127; 544/229; 544/362; 546/14; 546/135; 546/137

[58] Field of Search .................. 514/228.2, 235.2, 514/255, 305, 63; 544/61, 127, 362, 69, 229; 546/137, 14, 135

[56] References Cited

U.S. PATENT DOCUMENTS

| | | | |
|---|---|---|---|
| 5,242,930 | 9/1993 | Baker et al. | |
| 5,607,946 | 3/1997 | Kulagowski et al. | 514/312 |
| 5,620,971 | 4/1997 | Armistead et al. | 514/212 |
| 5,620,972 | 4/1997 | Van Niel | 514/213 |
| 5,620,976 | 4/1997 | Sugimoto et al. | 514/230.5 |
| 5,620,981 | 4/1997 | Blankley et al. | 514/258 |
| 5,620,989 | 4/1997 | Harrison et al. | 514/317 |
| 5,621,000 | 4/1997 | Arena et al. | 514/411 |
| 5,621,004 | 4/1997 | Dunn et al. | 514/551 |
| 5,621,140 | 4/1997 | Schloemer et al. | 562/401 |
| 5,622,236 | 4/1997 | Azumi et al. | 180/168 |
| 5,622,947 | 4/1997 | Ogawa et al. | 514/213 |
| 5,622,950 | 4/1997 | Baker et al. | 514/249 |
| 5,622,976 | 4/1997 | Takasugi et al. | 514/326 |
| 5,622,980 | 4/1997 | Caldwell et al. | 514/370 |
| 5,622,982 | 4/1997 | Schuster et al. | 514/399 |
| 5,622,983 | 4/1997 | Horwell et al. | 514/419 |
| 5,622,985 | 4/1997 | Olukotun et al. | 514/423 |
| 5,622,990 | 4/1997 | Katdare et al. | 514/533 |

FOREIGN PATENT DOCUMENTS

| | | |
|---|---|---|
| 0 499 313 | 8/1992 | European Pat. Off. |
| 9005729 | 5/1990 | WIPO |
| WO 92/20676 | 11/1992 | WIPO |
| WO 93/19064 | 9/1993 | WIPO |
| WO 94/10170 | 5/1994 | WIPO |

OTHER PUBLICATIONS

Cascieri et al., Characterization of the Interaction of N–Acyl–Tryptophan Benzyl Ester Neurokinin Antagonists with the Human Neurokinin–1 Receptor, The Journal of Biological Chemistry, vol.269, No. 9, pp. 6587–6591, Mar. 4, 1994.

MacLeod et al., N–Acyl–tryptophan Benzyl Esters: Potent Substance P Receptor Antagonists, Journal of Medicinal Chemistry, vol. 36, No. 14, pp. 2044–2045, Jul. 9, 1993.

*Primary Examiner*—Mukund J. Shah
*Assistant Examiner*—Brenda Coleman
*Attorney, Agent, or Firm*—Peter C. Richardson; Paul H. Ginsburg; Raymond M. Speer

[57] ABSTRACT

A compound of chemical formula (I) and its pharmaceutically acceptable salt:

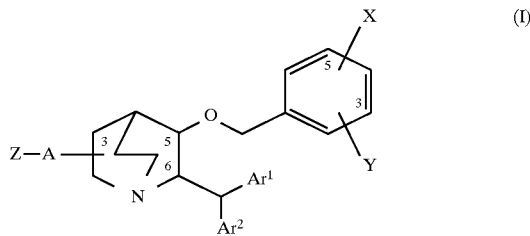

wherein X and Y are each hydrogen, halogen, $C_1$–$C_6$alkyl, halosubstituted $C_1$–$C_6$alkyl, $C_1$–$C_6$alkoxy, $C_1$–$C_6$alkylthio, $C_1$–$C_6$alkylsulfinyl, $C_1$–$C_6$alkylsulfonyl, or tri($C_1$–$C_6$alkyl)silyl; $Ar^1$ and $Ar^2$ are each independently aryl or heteroaryl, optionally substituted by halogen; A is —CO— or -($CH_2$)-; Z-A- is at the 2 or 3 position on the quinuclidine ring; and Z is —OH, $C_1$–$C_6$alkoxy, $NR^1R^2$ or the like. Representative compounds are (3S,4R,5S,6S)-5-[3,5-bis(trifluoromethyl)-benzyloxy]-N,N-dimethyl-6-diphenylmethyl-1-azabicyclo[2.2.2]octan-3-carboxamide, and -3-carboxylic acid. These novel benzyloxyquinuclidines are active as substance P receptor antagonists and are thus useful for treating gastrointestinal disorders, central nervous system disorders, allergy, inflammatory diseases, asthma, pain, emesis, migraine, urinary incontinence, or angiogenesis in mammals, especially humans.

18 Claims, No Drawings

BENZYLOXYQUINUCLIDINES AS SUBSTANCE P ANTAGONISTS

BACKGROUND OF THE INVENTION

This application is the U.S. national phase of PCT Patent Application PCT/JP94/01092, which was filed in the Japanese Receiving Office on Jul. 5, 1994.

This invention relates to novel and useful benzyloxyquinuclidines of interest to those in the field of medical chemistry and chemotherapy. More particularly, it is concerned with a novel series of benzyloxyquinuclidines, including their pharmaceutically acceptable salts and pharmaceutical composition thereof, which are of special value in view of their ability to antagonize substance P (SP). In this way, these compounds are of use in treating gastrointestinal disorders, central nervous system disorders, allergy, inflammatory diseases, asthma, pain, migraine, emesis, urinary incontinence and angiogenesis in mammalia.

Substance P is a naturally occurring undecapeptide belonging to the tachykinin family of peptides, the latter being so-named because of their prompt stimulatory action on smooth muscle tissue. More specially, substance P is a pharmaceutically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B. E. B. Sandberg et al., *J. Med. Chem.*, 25, 1009 (1982)), as well as in central nervous system disorders such as anxiety and schizophrenia, in respiratory and inflammatory diseases such as asthma and rheumatoid arthritis, respectively, and in gastrointestinal disorders and diseases of GI tract, like ulcerative colitis and Crohn's diseases, etc (see D. Regoli in "Trends in Cluster Headache" edited by F. Sicuteri et al., Elsevier Scientific Publishers, Amsterdam, 1987, PP. 85–95).

It is reported that the tachykinin antagonists are useful for allergic conditions (Hamelet et al., Can. J. Pharmacol. Physiol., 66, 1361, 1988), immunoregulation (Lotz et al., Science, 241, 1218, 1988; and Kimball et al., 3. Immunol., 141, 3564, 1988), vasodilation, bronchospasm, reflex or neuronal control of the viscera (Mantyh et al., PNAS, 85, 3235, 1988) and senile dementia of the Alzheimer type (Yankner et al., Science, 250, 279, 1990). Recently the efficacy of the substance P antagonists for the treatment of emesis (EP 0533280 A) and the relationship between substance P antagonists and sunburn (F. Gillardon et al, Involvement of neuropeptides and nitric oxide in the sunburn reaction following cutaneous ultraviolet irradiation. abstract 129, 1993, 5th Interscience World Conference on Inflammation, Antirheumatics, Analgesics, Immunomodulators, 1993, Geneva) are discussed.

In the recent past, some attempts to develop the tachykinin antagonist such as substance P have been carried out for the purpose of the treatment of the above disorders or diseases (John A Lowe, III, et al., Drugs of the Future, 17(12), 1115, 1992).

JP Kokai No. 78354/93 (EP-0499313A1) discloses a wide variety of azabicyclic compounds as tachykinin antagonists such as substance P antagonists, including a number of quinuclidine compounds having diarylmethyl and benzyloxy substituents. However, none of the individual compounds described in JP Kokai No. 78354/93 (EP-0499313A1) is a 6-diarylmethyl-5-benzyloxyquinuclidine having an additional substituent at the 2- or 3- position.

The purpose of the present invention is to provide the novel benzyloxyquinuclidines with substance P antagonistic activities. In addition, the purpose of the invention is also to provide a composition, which includes a benzyloxyquinuclidine as an active ingredient, in treating of gastrointestinal disorders, central nervous system disorders, allergy, inflammatory diseases, asthma, pain, migraine or emesis in mammalia, especially humans.

BRIEF DISCLOSURE OF THE INVENTION

The inventors made an effort in order to create compounds with substance P antagonistic activity. As a result, they discovered that specific benzyloxyquinuclidines and their pharmaceutically acceptable salts have excellent activity for the treatment of gastrointestinal disorders, central nervous system disorders, allergy, inflammatory diseases, asthma, pain migraine, emesis, urinary incontinence or angiogenesis, based on SP antagonistic activity.

The present invention relates to a compound of the chemical formula (I) and its pharmaceutically acceptable salt:

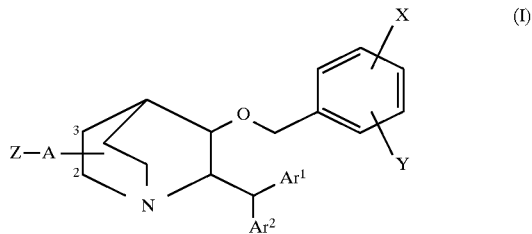

wherein X and Y are each hydrogen, halo, $C_1$–$C_6$ alkyl, halosubstituted $C_1$–$C_6$ alkyl, $C_1$–$C_6$ alkoxy, $C_1$–$C_6$ alkylthio, $C_1$–$C_6$ alkylsulfinyl, $C_1$–$C_6$ alkylsulfonyl or tri $C_1$–$C_6$ alkylsilyl;

$Ar^1$ and $Ar^2$ are each aryl optionally substituted by halo;

A is —CO— or -($CH_2$)-;

Z-A- is at 2 or 3 position on the quinuclidine ring;

Z is hydroxy, $C_1$–$C_6$ alkoxy, $NR^1R^2$ or $W^1$-($CH_2$)$_m$-$CHR^4$-($CH_2$)$_n$-$NR^3$-;

wherein $R^1$ and $R^2$ when taken separately are each hydrogen or $C_1$–$C_6$ alkyl;

$R^1$ and $R^2$ when taken together with the nitrogen atom to which they are attached represent piperidino, pyrrolidino, morpholino, thiomorpholino or piperazino;

$R^3$ is hydrogen, $C_1$–$C_6$ alkyl, benzyl or -($CH_2$)$_r$-$W^2$;

$R^4$ is hydrogen or $C_1$–$C_6$ alkyl which may be substituted by hydroxy, amino, methylthio, mercapto, benzyl, 4-hydroxybenzyl, 3-indolylmethyl or -($CH_2$)$_s$-$W^3$;

$R^3$ and $R^4$ when taken together represent $CH_2$ or $CH_2CH_2$;

$W^1$, $W^2$ and $W^3$ are each cyano, hydroxymethyl, $C_2$–$C_6$ alkoxymethyl, aminomethyl, ($C_1$–$C_6$ alkylamino)methyl, (di $C_1$–$C_6$ alkylamino)methyl, carboxyl, ($C_1$–$C_6$ alkyl) carbamoyl, or (di $C_1$–$C_6$ alkyl)carbamoyl, carbamoyl or ($C_1$–$C_6$ alkoxy)carbonyl; and m, n, r and s are each 0,1,2 or 3.

In this specification, the term "alkyl" is used to mean straight or branched hydrocarbon chain radicals including, but not limited to, methyl, ethyl, n-propyl, isopropyl, n-butyl, isobutyl, t-butyl, and the like;

the term "alkoxy" is used to mean —O-alkyl including, but not limited to, methoxy, ethoxy, propoxy, isopropoxy, n-butoxy, isobutoxy, t-butoxy and the like;

the term "halo" is used to mean radicals derived from the elements fluorine, chlorine, bromine and iodine;

the term "halosubstituted alkyl" is used to mean an alkyl radical substituted with one or more halogens including, but not limited to, chloromethyl, trifluoromethyl, 2,2,2-trichloroethyl and the like;

the term "halosubstituted alkoxy" is used to mean an alkoxy radical substituted with one or more halogens including, but not limited to, chloromethoxy, trifluoromethoxy, 2,2,2-trichloroethoxy and the like;

the term "alkylthio" is used to mean -S-alkyl including, but not limited to, methylthio, ethylthio, n-propylthio, isopropylthio, n-butylthio, isobutylthio, t-butylthio and the like;

the term "alkylsulfonyl" is used to mean —SO-alkyl including, but not limited to, methylsulfonyl, ethylsulfonyl, isopropylsulfonyl and the like;

the term "alklsulfonyl" is used to mean —SO$_2$-alkyl including, but not limited to, methylsulfonyl, ethylsulfonyl, isopropylsulfonyl and the like; and the term "aryl" is used to mean aromatic radicals including, but not limited to, phenyl, naphthyl, pyridyl, quinolyl, thienyl, furyl, oxazolyl, tetrazolyl, thiazolyl, imidazolyl, pyrazolyl and the like. These aryl groups can be substituted by $C_1$–$C_6$ alkyl, $C_1$–$C_6$ alkoxy, $C_1$–$C_6$ alkylthio, halogen, cyano, nitro, phenoxy, mono- or di-$C_1$–$C_6$ alkylamino and the like.

In the compounds of formula I of the invention, the preferred position of the substituent Z-A- on the quinuclidine ring is the 3-position, and the preferred configuration is 3R,4S or 3S,4R. S is preferable for the configuration of both benzyloxy at 5 position and diarylmethyl at 6 position.

Preferred compounds of the present invention are those having structure of formula (I) wherein $Ar^1$ and $Ar^2$ are phenyl; Z-A- is at the 3-position, A is —CO—; Z is —OH, —OCH$_3$, —NR$_1$R$_2$ (wherein R$_1$ and R$_2$ are each —H, —CH$_3$ or —CH$_2$CH$_3$), morpholino or NH$_2$COCH$_2$NH—; X is hydrogen, 3-CH$_3$, 3-CF$_3$ or 3-F; and Y is 5-CH$_3$, 5-CF$_3$ or 5-F.

The present invention further relates to a group of preferred compounds of chemical formula (I-a) and pharmaceutically acceptable salt forms thereof, comprising:

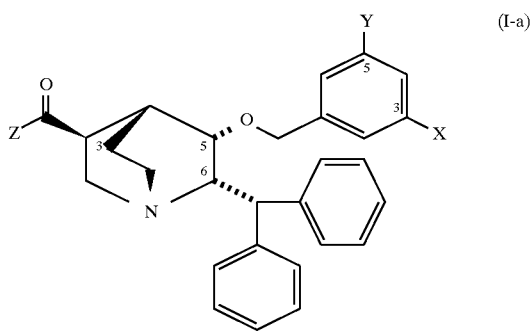

wherein

X is independently selected from the group consisting of —H, —F, —CH$_3$, and —CF$_3$; Y is independently selected from the group consisting of —F, —CH$_3$, and —CF$_3$; and Z is independently selected from the group consisting of —NR$^1$R$^2$, where R$^1$ and R$^2$ are each independently —H, —CH$_3$, or —CH$_2$CH$_3$ ; as well as together with a pharmaceutically acceptable carrier therefor to form a pharmaceutical composition. Said compounds and pharmaceutical compositions are useful in a method of treating or preventing in a mammalian subject, a condition at least partially mediated by substance P, associated with an excess of substance P activity, and responding favorably to significant antagonism of substance P receptors, wherein said condition is emesis, or said condition is a central nervous system disorder comprising one or more members selected from the group consisting essentially of anxiety, depression, dysthymic disorders, psychosis, pain, migraine, addiction disorders, alcoholism, neuropathological disorders, and Alzheimer's disease, comprising administering to said subject an amount therapeutically effective to treat or prevent said emesis or said central nervous system disorder.

Preferred compounds of the present invention are:

(3S,4R,5S,6S)-N-carbamoylmethyl-6-diphenylmethyl-5-(3,5-bis(trifluoromethyl)benzyloxy)-1-azabicyclo[2.2.2]octane-3-carboxamide;

(3S,4R,5S,6S)-6-diphenylmethyl-5-(3,5-bis(trifluoromethyl)benzyloxy)-1-azabicyclo[2.2.2]octane-3-carboxamide;

(3S,4R,5S,6S)-N,N-(3-oxa-1,5-pentylene)-6-diphenylmethyl-5-(3,5-bis(trifluoromethyl)benzyloxy)-1-azabicyclo[2.2.2]octane-3-carboxamide;

(3S,4R,5S,6S)-6-diphenylmethyl-5-(3,5-dimethylbenzyloxy)-1-azabicyclo[2.2.2])octane-3-carboxylic acid;

(3S,4R,5S,6S)-N,N-diethyl-6-diphenylmethyl-5-(3,5-bis(trifluoromethyl)benzyloxy)-1-azabicyclo[2.2.2]octane-3-carboxamide;

(3S,4R,5S,6S)-6-diphenylmethyl-5-(3-fluoro-5-trifluoromethylbenzyloxy)-1-azabicyclo[2.2.2]octane-3-carboxylic acid;

(3S,4R,5S,6S)-6-diphenylmethyl-5-(3,5-bis(trifluoromethyl)benzyloxy)-1-azabicyclo[2.2.2])octane-3-carboxylic acid; and (3S,4R,5S,6S)-N,N-dimethyl-6-diphenylmethyl-5-(3,5-bis(trifluoromethyl)benzyloxy)-1-azabicyclo[2.2.2]octane-3-carboxamide.

The compounds of formula (1) form acid addition salts and these salts are within the scope of this invention. The pharmaceutically acceptable acid addition salts are those formed from acids which form non-toxic acid salts.

The present invention includes pharmaceutical compositions for treatment or prevention of a condition at least partially mediated by substance P, associated with an excess of substance P activity, and responding favorably to significant antagonism of substance P receptors, wherein said condition is selected from the group consisting of inflammatory diseases (e.g, arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic disease such as angina, migraine and Raynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, rheumatic diseases such as fibrositis, sunburn, emesis, urinary incontinence and angiogenesis in a mammal, including a human, which comprise a pharmaceutically acceptable carrier or diluent and a compound of the formula (I) or a pharmaceutically acceptable salt thereof.

This invention relates to the therapeutic method which comprises administering to a mammal, especially a human, a therapeutically effective amount of a compound of the formula (I) or its pharmaceutically acceptable salt in order to treat or prevent the above diseases.

This invention also provides a compound of the formula:

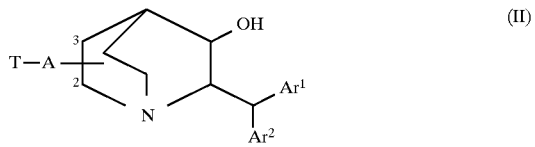

wherein $Ar^1$, $Ar2$ and A are as previously defined;

T-A- is at 2 or 3 position on the quinuclidine ring; and

T is hydroxy, $C_1$–$C_6$ alkoxy, $NR^1R^2$ wherein $R^1$ and R2 are as previously defined or benzyloxy optionally substituted with one or two substituents selected from $C_1$–$C_6$ alkyl, $C_1$–$C_6$ alkoxy and halosubstituted $C_1$–$C_6$ alkyl. These compounds of formula (II) are useful as intermediates to prepare the compounds of formula (I).

Further, this invention provides a process for preparing the intermediate compounds of formula (II), which comprises the following steps:

(a) subjecting a compound of the formula:

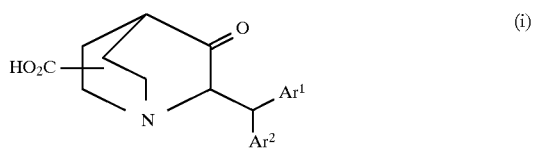

to amidation to obtain a compound of the formula:

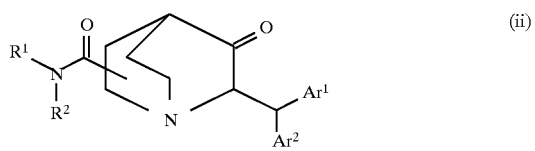

and then (b) reducing the compound (ii) in the presence of a reducing agent.

The present invention also provides another method to prepare the above-mentioned intermediate compounds, which comprises the following steps:

(a) reducing, in the presence of a reducing agent, a compound of the formula:

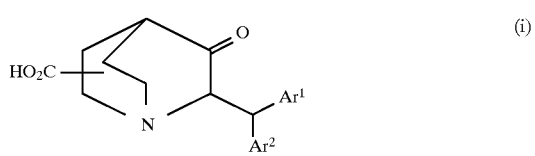

to obtain a compound of the formula:

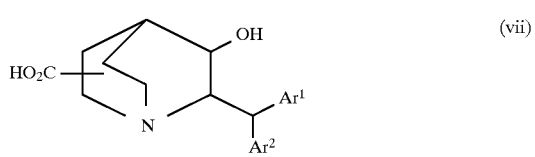

and then (b) subjecting the compound (vii) to esterification.

Furthermore, the present invention provides a process for preparing a compound of formula (I), which comprises the following steps:

(a) reacting a compound of the formula:

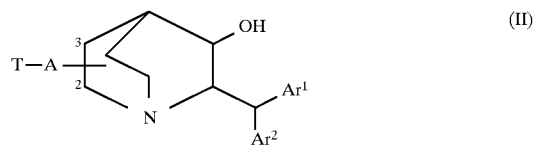

with a benzylating agent to obtain a compound of the formula:

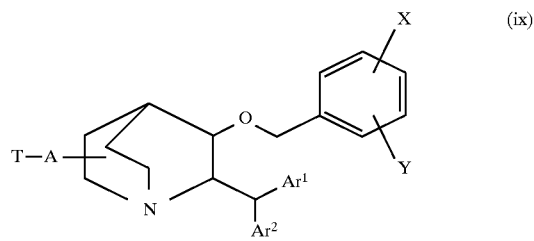

(b) hydrolyzing or reducing the compound (ix) to obtain a compound of the formula: X

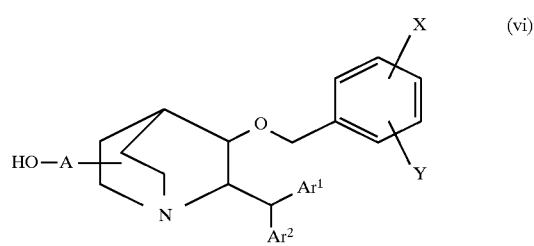

and, if desired (c) converting the carboxyl group or the hydroxymethyl group of the compound (vi) to a desired group. In the preferred process, compound (ix) wherein T-A- is benzyloxycarbonyl can be obtained by benzylation of compound (II) wherein T-A- is carboxy.

DETAILED DISCLOSURE OF THE INVENTION

The novel benzyloxyquinuclidines (I) of this invention may be prepared by a number of synthetic methods well known to those skilled in the art.

Thus, the following Route 1 and Route 2 are available to prepare the objective compounds of the present invention:

Route 1

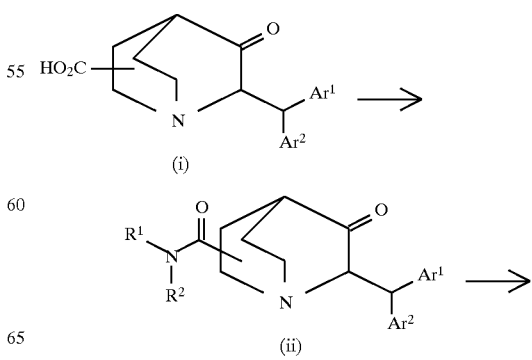

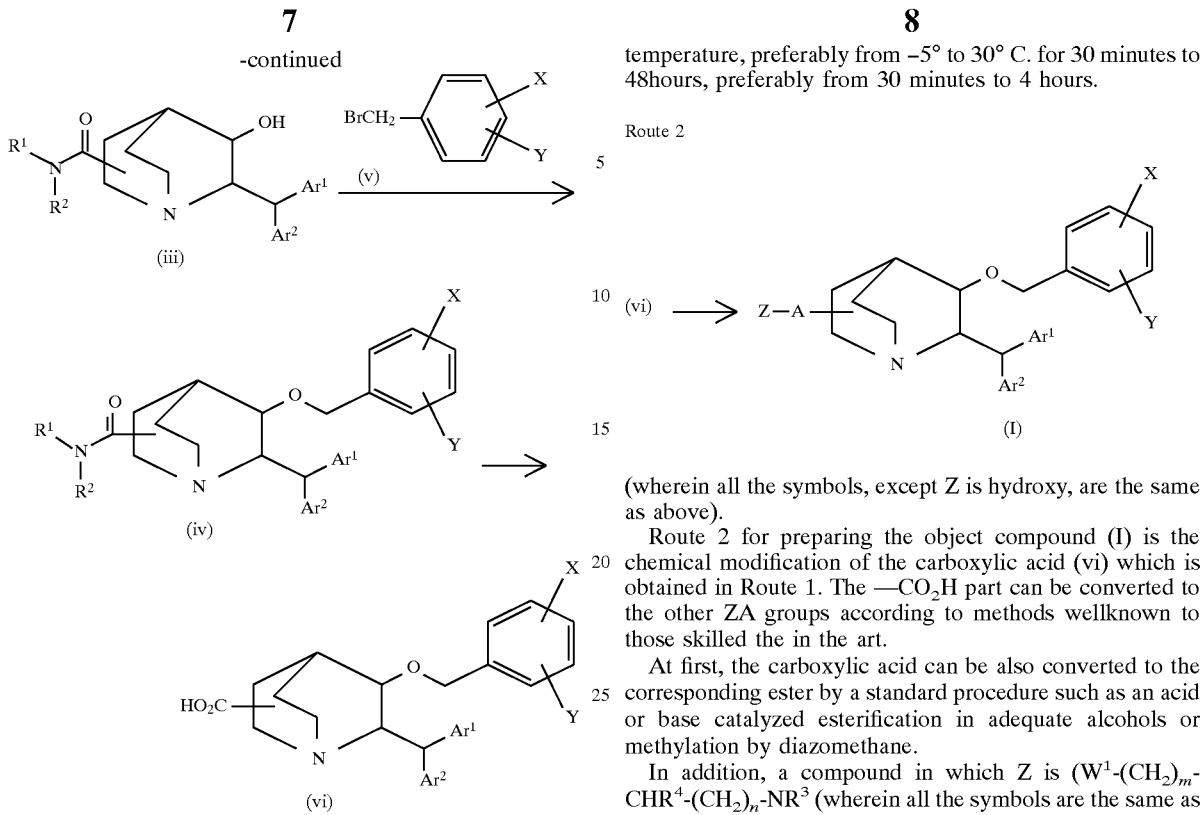

(wherein all the symbols are as previously defined).

Route 1 is a method through amidation of 6-diarylmethyl-2(or3)-carboxyquinuclidine-5-one (i) and reduction followed by benzylation. The amide (iv) is easily hydrolised to carboxylic acid (vi). In addition, compound (iii) corresponds to the intermediate compound of formula (II) wherein T-A- is $C(O)NR^1R^2$.

In this route, the transformation from carboxylic acid (i) to amide (ii) can be used by, for example, $(EtO)_2POCN$-amine ($NHR^1R^2$), $ClCO_2Et$-$NHR^1R^2$ or the condensation method with $NHR^1R^2$ using DCC (dicyclohexylcarbodiimide) or WSC (water solble carbodiimide) in the inert solvent such as dimethylformamide (DMF) and tetrahydrofuran (THF). The amidation can be carried out at a temperature of from −78° C. to reflux temperature, preferably from −5° to 30° C. for 5 minutes to 48 hours, preferably from 60 minutes to 18 hours. In the next step, the carbonyl group at 5 position is derived to the compound (iii) by reduction.

The appropriate reduction agents such as sodium borohydride in methanol in this reduction. Especially $LiBEt_3H$ in DME for the cis selective reduction and Na in isopropanol for trans selective reduction (EP-0499313A1; E. M. Seward et al., Bio. Med. Chem. Lett., 6, 1361, 1993) are convenient respectively. The reduction can be carried out at a temperature of from −78° to 30° C., preferably from −5° to 30° C. for 5minutes to 48 hours, preferably from 60 minutes to 2 hours.

Benzyl compound (iv) can be obtained by reacting alcohol (iii) with benzyl bromide in the presence of a base. The preferable bases in the benzylation are $^t$-BuOK, NaH, KH, KOH, BuLi, LDA and the like. The crown-ethers such as 18-crown-6 can be added to the reaction if needed. Benzyl chloride, benzyl iodide, benzyl triflate, benzyl mesylate and the like can be used as benzylating agents. The benzylation can be carried out at a temperature of from −78° C. to reflux temperature, preferably from −5° to 30° C. for 30 minutes to 48hours, preferably from 30 minutes to 4 hours.

(wherein all the symbols, except Z is hydroxy, are the same as above).

Route 2 for preparing the object compound (I) is the chemical modification of the carboxylic acid (vi) which is obtained in Route 1. The $—CO_2H$ part can be converted to the other ZA groups according to methods wellknown to those skilled the in the art.

At first, the carboxylic acid can be also converted to the corresponding ester by a standard procedure such as an acid or base catalyzed esterification in adequate alcohols or methylation by diazomethane.

In addition, a compound in which Z is $(W^1$-$(CH_2)_m$-$CHR^4$-$(CH_2)_n$-$NR^3$ (wherein all the symbols are the same as already defined) in the side chain Z—CO— on the quinuclidine ring can be synthesized by a various conventional methods for peptide synthesis as described in "Peptide synthesis, the basis and experiments" edited by N. Izumiya, 1985 (Maruzen).

For instance, those methods include an activated ester method with acid chloride or mixed acid anhydride, and a condensation method employing an appropriate condensing agent which is selected from dicyclohexylcarbodiimide (DCC), water soluble carbodiimide, 2-ethoxy-N-ethoxycarbonyl-1,2-dihydroquinoline, Bop agent (Benzotriazol-1-yloxy-tris(dimethylamino) phosphonium hexafluorophosphate), diethyl azodicarboxylate-triphenylphosphine, diethylcyanophosphonic acid and diphenylphospholylazide and the like. A reaction-inert solvent such as dichloromethane, THF, dimethylformamide and toluene are suitable in the condensation reaction. If necessary, addition of tertiary amine such as triethylamine can promote the condensation reaction. Furthermore, in order to prevent racemization, employment of N-hydroxy succinimide, N-hydroxybenzotriazole or 3,4-dihydro-3-hydroxy-4-oxo-1,2,3-benzotriazine etc. can bring a preferable result in this reaction. In general, the esterification can be carried out at from −78° to reflux temperature, preferably from −5° to 30° C. for 5 minutes to 48 hours, preferably from 60 minutes to 18 hours.

If OH or NH part interferes the transformation, appropriate protection of OH or NH group is necessary. A suitable protective group can be chosen from a variety of known protective groups such as benzyloxycarbonyl (Cbz), t.-butyloxycarbonyl (Boc) and trialkylsilyl (c.f. T. W. Greene, "Protective Groups in Organic Synthesis", J. Wiley & Sons (1981)). After finishing transformation of the functional group, the protecting group is removed by a suitable standard procedure to provide the objective compound.

Conversion of compound (vi) into a compound of formula (I) having the other Z-A- groups can be carried out by methods well-known in the art. See, for example, PCT/

US90/05729, PCT/US92/20676 and JP application No. 307179/92. These method can be used, for example, when side chain (Z-A-) on the quinuclidine ring is methoxycarbonyl, carbamoyl, ethylaminocarbonyl, N-methoxy-N-methylaminocarbonyl, dimethylaminocarbonyl, diethylaminocarbonyl, morpholinocarbonyl, thiamorpholinocarbonyl, (4-thiamorpholino-4-oxo)carbonyl, (4-thiamorpholino-4,4-dioxo)carbonyl, carboxy, N-(2-carbamoylpyrrolidin-1-yl) carbonyl, N-(1-carbamoylmethyl)carbamoyl, N-(1-carbamoylethyl)carbamoyl, N-(1-carbamoyl-3-methylbutyl) carbamoyl, N-(2-carbamoylethyl)carbamoyl, N-(1-carbamoyl-2-phenethyl)carbamoyl, N,N-bis(cyanomethyl)carbamoyl.

In addition, as an alternative method to Route 1, the following Route 1A may be used.

Route 1A

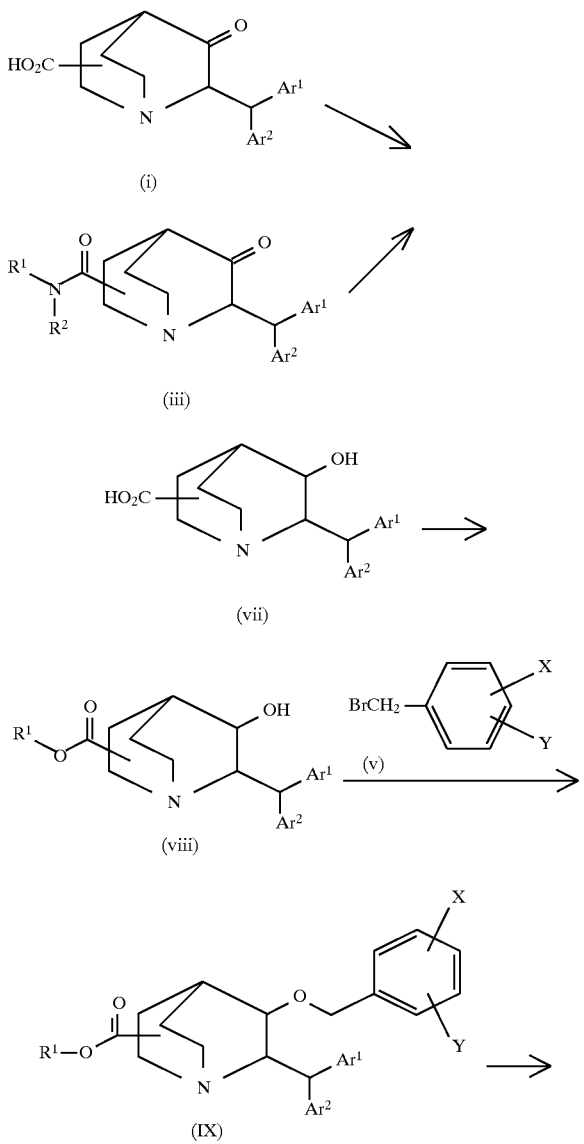

-continued

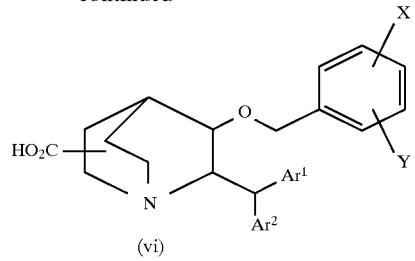

Route 1A is a method through reduction of 6-diarylmethyl-2(or 3)-carboxyquinuclidine-5-one (i) or hydrolyzation of compound (iii), and esterification followed by benzylation. The ester (ix) can be easily derived to carboxylic acid (vi). In addition, compound (viii) corresponds to the intermediate compound of formula (II) wherein T-A- is —C(O)OR$^1$. In this route, the reduction of ketone (i) to compound (vii) may be carried out in a similar manner to the reduction of compound (ii) as described in Route 1 above. For example, the reduction may be carried out in the presence of an appropriate reducing agent such as sodium borohydride or sodium triacetoxyborohydride in a reaction-inert solvent such as methanol, ethanol, tetrahydrofuran, methylene chloride or acetic acid. Also, compound (vii) can be also prepared by hydrolyzation of compound (iii). Carboxylic acid (vii) can be converted to the corresponding ester (viii) by a standard procedure as described in Route 2 above. Benzyl compound (ix) can be obtained by reacting ester (viii) with a benzylating agent under similar conditions to those described in Route 1 above. Alternatively, Compound (ix) can be directly obtained by benzylation of Compound (vii) if R$^1$ is benzyl or substituted benzyl such as alkylbenzyl or alkoxybenzyl. If desired, Compound (ix) can be easily hydrolyzed to obtain compound (vi). Suitable methods for the hydrolyzation are described in T. W. Greene, "Protective Groups in Organic Synthesis", J. Wiley & Sons (1981)). In addition, Compound (ix) wherein R$^1$ is benzyl or the substituted benzyl as mentioned above, can be subjected to hydrogenolysis using a metallic catalyst such as palladium on carbon in alcohol such as methanol, ethanol or isopropylalcohol, to obtain Compound (vi).

The reaction used in the above general synthesis can be easily monitored by thin-layer chromatography (TLC).

The compounds of formula (I) and the various intermediates described in the general syntheses can be isolated and purified by conventional procedures, such as recrystallisation or chromatography.

As the quinuclidine compounds of this invention all possess at least two asymmetric centers, they are capable of occurring in various stereoisomeric forms or configurations. Hence, the compounds can exist in separated (+)- and (-)-optically active forms, as well as in racemic or (±)-mixtures thereof. The present invention includes all such forms within its scope. For instance, the diastereomers can be obtained by methods well known to those skilled in the art, e.g., by separation of mixtures by fractional crystallization or chromatographic separation, asymmetric synthesis and the like. Hence, when those skilled in the art use the compounds of this invention, they may choose any desired isomers, such as optical isomers and diastereomers, or mixtures thereof, from among the objective compounds of the present invention according to their application purpose.

Insofar as the quinuclidine compounds of this invention are basic compounds, they are all capable of forming a wide variety of salts with various inorganic and organic acids.

Although such salts must be pharmaceutically acceptable for administration to animals, it is often desirable in practice to initially isolate the quinuclidine base compound from the reaction mixture as a pharmaceutically unacceptable salt and then simply convert to the free base compound by treatment with an alkaline reagent and thereafter, subsequently convert the free base to a pharmaceutically acceptable acid addition salt. The acid addition salts of the quinuclidine base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained.

The acid which are used to prepare the pharmaceutically acceptable acid addition salts of the aforementioned quinuclidine base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, ptoluenesulfonate and pamoate (i.e., 1.1'-methylene-bis-(2-hydroxy-3-naphthoate))salts. The quinuclidine compounds of the invention which have also acidic groups are capable of forming base salts with various pharmaceutically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic quinuclidine derivatives. These particular non-toxic base salts include those derived form such pharmaceutically acceptable cations as sodium, potassium, calcium and magnesium, etc. These salts can easily be prepared by treating the aforementioned acidic quinuclidine compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The quinuclidine compounds of the formula I exhibit significant substance P receptor-binding activity and therefore, are of value in the treatment of a wide variety of clinical conditions which are characterized by the presence of an excess of said substance P activity and respond favorably to significant antagonism of substance P receptors. Such conditions include gastrointestinal disorders such as ulcer and colitis and other like diseases of the gastrointestinal tract, central nervous system disorders such as anxiety and psychosis, inflammatory diseases such as rheumatoid arthritis and inflammatory bowel diseases, respiratory diseases such as asthma, allergy, emesis, sunburn, as well as pain in any of the aforesaid conditions, including migraine. Hence, these compounds are readily adapted to therapeutic use as substance P antagonists for the control and/or treatment of any of the aforesaid clinical conditions in mammals, including humans.

The activity of the compounds of the present invention, as substance P antagonists, is determined by their ability to inhibit the binding of substance P at its receptor sites in CHO-cells which reveal NK1 receptor or IM-9 cells employing radioactive ligands. The substance P antagonist activity of the herein described quinuclidine compounds is evaluated by using the standard assay procedure described by M. A. Cascieri et al., as reported in the *Journal of Biological Chemistry*, 258, 5158 (1983). This method essentially involves determining the concentration of the individual compound required to reduce by 50% the amount of radiolabelled substance P ligands at their receptor sites in said isolated cow tissues or IM-9 cells, thereby affording characteristic $IC_{50}$ values for each compound tested. In this test, some preferred compounds indicated low $IC_{50}$ values of less than 0.1 nM with respect to inhibition of binding at its receptor.

The compounds of the present invention, when tested as an antiinflammatory agent, exhibit a significant degree of activity in the mustard oil-induced rat foot edema test [described by F. Lembeck et al., *British Journal of pharmacology*, 105, 527 (1992)].

Alternatively, the antiinflammatory activity of the compounds of the present invention is demonstrated by a capsaicin-indused plasma extravasation test. In this test, antiinflammatory activity is determined as the percent inhibition of plasma protein extravasation in the ureter of male Hartley quinea pigs (weighing 300–350 g) in response to the intraperitoneal injection of capsaicin into anesthetized animals. The compounds of the present invention are dissolved in 0.1% methyl cellulose/water and dosed orally 1 h before capsaicin challenge. Evans Blue dye (30 mg/kg) is administered intravenously 5 min before capsaicin challenge. The animals are killed 10 min after capsaicin injection and both right and left ureters are removed. The Evans Blue dye is extracted and determined calorimetrically. In the above tests, compounds are considered active if the difference in response between the drug-treated animals and a control group receiving the vehicle alone is statistically significant.

According to the capsaicin-induced plasma extravasation test the compounds of formula (I) of this invention show surprisingly high activity. For example, the $ED_{50}$ of the compound in example 2 was more than 100 times lower than the $ED_{50}$ of the non-substituted compound (x) disclosed in JP Kokai 78354/93 (EP-0499313A1) was 2.4 mg/kg.

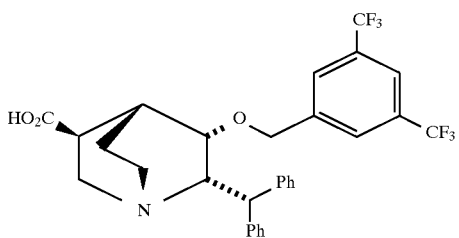

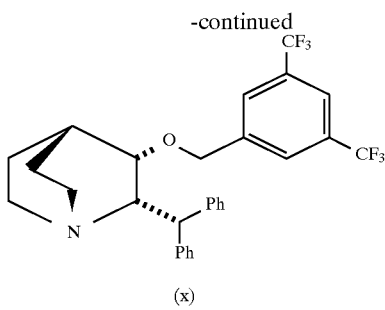

(x)

Example 2

Z-A-=$CO_2H$

The anti-psychotic activity of the compounds of the present invention as neuroleptic agents for the control of various psychotic disorders is determined primarily by a study of their ability to suppress substance P-induced hypermotility in rats. This study is carried out by first dosing the rats with a control compound or with an appropriate test compound of the present invention, then injecting the rats with substance P by intracerebral administration via canula and thereafter measuring their individual locomotor response to said stimuli.

The radiolabelled quinuclidine compounds of the formula I are useful as research and diagnostic tools in metabolism pharmacokinetic studies and in binding assays with the drug in both animal and human. Specific applications in research include radioligand binding assays, autoradiography studies and in vivo binding studies, while specific applications in the diagnostic area include studies of substance P receptor in the human brain, such as up/down regulation in a diseases state, and in vivo binding in the relevant tissues for inflammation, e.g., immune-type cell or cells that are directly involved in inflammatory bowel disorders and the like. Specifically, the radiolabelled forms of the quinuclidine compounds are the tritium and $^{14}C$-isotopes of substituted benzyloxyquinuclidine in this invention.

The quinuclidine compounds of the formula (I) of this invention can be administered via either the oral, parenteral or topical routes to mammals. In general, these compounds can be administered to humans in doses ranging from about 0.3 mg up to 750 mg per day. Variations will necessarily occur depending upon the weight of the subject being treated, the particular route of administration, the disease state of the subject being treated and the activity of the particular compound chosen. However, a dosage level that is in the range of from about 0.06 mg to about 2 mg per kg of body weight per day is most desirably employed for treatment or prevention of an inflammatory, pain, and emesis condition in a human subject.

The compounds of the present invention may be administered alone or in combination with pharmaceutically acceptable carriers or diluents by any of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The present invention is illustrated by the following examples. However, it should be understood that the invention is not limited to the specific details of these examples. $^1H$ and $^{13}C$ nuclear magnetic resonance spectra (NMR) were measured in $CDCl_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

Example 1

(3S,4R,5S,6S)-5-(3,5-bis(trifluoromethy)1benzyoxy)-N,N-dimethyl-6-diphenylmethyl-1-azabicyclo[2.2.2]octane-3-carboxamide.

(i)(3S,4R,6S)-5-Oxo-6-diphenylmethyl-1-azabicyclo[2.2.2]octane-3-carboxamide

A suspension of (3S,4R)-5-oxo-6-diphenylmethyl-1-azabicyclo[2.2.2]octane-3-carboxylic acid hydrochloride (5 g, 13.5 mmol) in THF (50 ml) was treated with triethylamine (4.1 g, 40 mmol) at room temperature. To this suspension was added ethyl chloroformate (2.9 g, 27 mmol) at 0° C. After 30 min, $NH_3$ aq (50 ml) was added at 0° C. The mixture was stirred at room temperature for 12 hr. The solvent was removed. The crude was purified by recrystallization from MeOH to give title compound (2.2 g, 6.6 mmol, 49%).

$^1$H NMR δ 7.47–7.15 (m, 10H), 5.39 (br, 2H), 4.54 (d, J=12Hz, 1H), 3.97 (d, J=12Hz, 1H), 3.28–2.96 (m, 3H), 2.73–2.55 (m, 3H), 2.32–2.14 (m, 1H), 1.93–1.80 (m, 1H).

(ii)(3S,4R,5S,6S)-5-Hydroxy-6-diphenylmethyl-1-azabicyclo[2.2.2]octane-3-carboxamide To a solution of (3S,4R,6S)-5-oxo-6-diphenylmethyl-1-azabicyclo[2.2.2]octane-3-carboxamide (obtained in Example 1 (i); 2.0 g, 6 mmol) in DME (50 ml) was added lithium triethylborohydride (8 ml, 8 mmol; 1M in THF) at 0° C. The mixture was stirred at 0° C. for 15 min. After addition of 1N HCl (10 ml), the solution was concentrated. The residue was dissolved in CH$_2$Cl$_2$ (30 ml) and NaOH aq (10 ml) then extracted with CH$_2$Cl$_2$ three times. The combined extracts were dried over Na$_2$SO$_4$ and concentrated. The crude was purified by recrystallization from MeOH (10 ml) to give title compound (1.6 g, 4.8 mmol, 80%) as a colorless crystal.

$^1$H-NMR δ 7.50–7.18 (m, 10H), 5.45 (br, 1H), 5.32 (br, 1H), 4.40 (d, J=12Hz, 1H), 4.11–4.03 (m, 1H), 3.67 (dd, J=12, 7Hz, 1H), 3.19 (d, J=6Hz, 1H), 3.04–2.90 (m, 2H), 2.74–2.62 (m, 1H), 2.24–2.17 (m, 1H), 1.88–1.76 (m, 1H), 1.50 (d, J=3Hz, 1H), 1.45–1.30 (m, 1H).

(iii)(3S,4R,5S,6S)-5-Hydroxy-6-diphenylmethyl-1-azabigyclo[2.2.2]octane-3-carboxylic acid A solution of (3S,4R,5S,6S)-5-hydroxy-6-diphenylmethyl-1-azabicyclo[2.2.2]octane-3-carboxamide (obtained in Example 1 (ii); 1.3 g, 3.9 mmol) in conc. HCl (10 ml) was heated at reflux for 3 hr. The resulting precipitate was collected and dried to give title compound (1.3 g, quant.). This was used without further purification.

$^1$H-NMR (DMSO-d$_6$) δ 8.70 (br, 1H), 7.66–7.12 (m, 10H), 6.14 (br, 1H), 4.87 (br, 1H), 4.64 (d, J=12Hz, 1H), 4.15–1.60 (m, 10H)

(iv)(3S,4R,5S,6S)-5-Hydroxy-N,N-dimethyl-6-diphenylmethyl-1-azabicyclo[2.2.2]octane-3-carboxamide A suspension of (3S,4R,5S,6S)-5-hydroxy-6-diphenylmethyl-1-azabicyclo[2.2.2]octane-3-carboxylic acid (obtained in Example 1 (iii); 0.19 g, 0.5 mmol) and dimethylamine hydrochloride (0.06 g, 0.7 mmol) in DMF (2 ml) was treated with triethylamine (0.11 g, 1.1 mmol) at room temperature. To this suspension was added diethyl cyanophosphonate (0.11 g, 0.6 mmol) followed by triethylamine (0.07 g, 0.6 mmol) at room temperature. The mixture was stirred at room temperature for 5 hr, poured into 0.2N NaOH (10 ml) and extracted with CH$_2$Cl$_2$ three times. The combined extracts were dried over Na$_2$SO$_4$ and concentrated to give title compound (0.18 g, 0.5 mmol, quant.). This was used without further purification.

$^1$H NMR δ 7.50–7.10 (m, 10H), 4.43 (d, J=12Hz, 1H), 4.10–4.03 (m, 1H), 3.71 (dd, J=12, 7Hz, 1H), 3.42–2.87 (m, 4H), 3.00 (s, 3H), 2.94 (s, 3H), 2.72–2.60 (m, 1H), 1.83–1.26 (m, 3H).

(v)(3S,4R,5S,6S)-5-(3,5-Bis(trifluoromethyl)benzyoxy)-N,N-dimethyl-6-diphenylmethyl-1-azabicyclo[2.2.2]octane-3-carboxamide To a suspension of (3S,4R,5S,6S)-5-hydroxy-N,N-dimethyl-6-diphenylmethyl-1-azabicyclo[2.2.2]octane-3-carboxamide (obtained in Example 1 (iv); 80 mg, 0.25 mmol) in DME (3 ml) was added potassium t-butoxide (40 mg, 0.3 mmol) followed by 18-crown-6 (70 mg, 0.3 mmol) at 0° C. To this solution was added 3,5-bis(trifluoromethyl) benzyl bromide (90 mg, 0.3 mmol) in DME (1 ml) at 0° C. The mixture was stirred at 0° C. for 1 hr, quenched with H$_2$O (10 ml), and extracted with CH$_2$Cl$_2$ three times. The combined extracts were dried over Na$_2$SO$_4$ and concentrated. The crude was purified by recrystallization from MeOH (1 ml) to give title compound (53 mg, 0.09 mmol, 36%)

$^1$H-NMR δ 7.78–7.10 (m, 13H), 4.40 (d, J=12Hz, 1H), 4.17 (d, J=12Hz, 1H), 3.92–3.70 (m, 2H), 3.52 (d, J=12Hz, 1H), 3.28–2.63 (m, 5H), 2.95 (s, 3H), 2.93 (s, 3H), 2.00–1.86 (m, 1H), 1.43–1.30 (m, 1H).

Example 2

(3S,4R,5S,6S)-3,5-bis(trifluoromethyl)benzyoxy)-6-diphenylmethyl-5-(-1-azabicyclo[2.2.2]octane-3-carboxylic acid hydrochloride.

A solution of (3S,4R,5S,6S)-5-(3,5-bis(trifluoromethyl) benzyoxy)-N,N-dimethyl-6-diphenylmethyl-1-azabicyclo [2.2.2]octane-3-carboxamide (obtained in Example 1 (v); 18 mg, 0.03 mmol) in conc. HCl (1 ml) was heated at reflux for 6 hr. The resulting precipitate was collected and dried to give title compound (11 mg, 0.02 mmol, 61%).

$^1$H-NMR (DMSO-d$_6$) δ 8.20–7.10 (m, 13H), 5.20–5.06 (m, 1H), 4.65 (d, J=12Hz, 1H), 4.58 (d, J=12Hz, 1H), 4.20–2.88 (m, 9H), 2.07–1.76 (m, 2H).

Example 3

(3S,4R,5S,6S)-N,N-Dimethyl-5-(3,5-dimethylbenzyoxy)-6-diphenylmethyl-1-azabicyclo[2.2.2]octane-3-carboxamide To a suspension of (3S,4R,5S,6S)-5-hydroxy-N,N-dimethyl-6-diphenylmethyl-1-azabicyclo[2.2.2]octane-3-carboxamide (obtained in Example 1 (iv); 400 mg, 1.1 mmol) in DME (15 ml) was added potassium t-butoxide (150 mg, 1.3 mmol) followed by 18-crown-6 (300 mg, 1.2 mmol) at 0° C. To this solution was added 3,5-dimethylbenzyl bromide (260 mg, 1.3 mmol) in DME (1 ml) at 0° C. The mixture was stirred at 0° C. for 3 hr, quenched with H$_2$O (20 ml), and extracted with CH$_2$Cl$_2$ three times. The combined extracts were dried over Na$_2$SO$_4$ and concentrated. The crude was purified by a column chromatography on silica gel to give title compound (470 mg, 0.97 mmol, 88%).

$^1$H-NMR δ 7.40–7.07 (m, 10H), 6.88 (br, 1H), 6.51 (br, 2H), 4.46 (d, J=12Hz, 1H), 3.89–3.57 (m, 4H), 3.27–3.00 (m, 4H), 2.92 (s, 3H), 2.88 (s, 3H), 2.74–2.60 (m, 1H), 2.26 (s, 6H), 2.20 (br, 1H), 1.84–1.25 (m, 2H).

Example 4

(3S,4R,5S,6S)-N-Carbamoylmethyl-6-diphenylmethyl-5-(3,5-bis(trifluoromethyl)benzyoxy)-1-azabicyclo[2.2.2] octane-3-carboxamide A suspension of (3S,4R,5S,6S)-6-diphenylmethyl-5-(3,5-bis(trifluoromethyl)benzyoxy)-1-azabicyclo[2.2.2]octane-3-carboxylic acid hydrochloride (obtained in Example 2; 120 mg, 0.2 mmol) and glycinamide hydrochloride (30 mg, 0.25 mmol) in DMF (1 ml) was treated with triethylamine (30 mg, 0.3 mmol) at room temperature. To this suspension was added 3-dimethylaminopropyl ethyl carbodiimide (70 mg, 0.35 mmol) at room temperature. The mixture was stirred at room temperature for 18 hr, poured into 2N NaOH aq and extracted with CH$_2$Cl$_2$ three times. The combined extracts were dried over Na$_2$SO$_4$ and concentrated to give oil, which was purified by a column chromatography on silicagel to give a solid (30 mg, 0.05 mmol, 27%)

$^1$H NMR (CDCl$_3$) δ 7.77 (br, 1H), 7.50–7.05 (m, 12H), 6.44 (br, 1H), 6.18 (br, 1H), 5.59 (br, 1H), 4.43–4.30 (m, 2H), 4.00–2.62 (m, 10H), 2.45 (br, 1H), 1.90–1.30 (m, 2H).

Elemental Analysis (1.5 H$_2$O) for C$_{32}$H$_{31}$N$_3$O$_3$F$_6$:

Calcd. C: 59.44% H: 5.30% N: 6.50%

Found C: 59.47% H: 5.31% N: 6.22%

Example 5
(3S,4R,5S,6S)-6-Diphenylmethyl-5-(3,5-bis (trifluoromethyl)benzyoxy)-1-azabicyclo[2.2.2]octane-3-carboxamide A suspension of (3S,4R,5S,6S)-6-diphenylmethyl-5-(3,5-bis(trifluoromethyl)benzyoxy)-1-azabicyclo[2.2.2]octane-3-carboxylic acid hydrochloride (obtained in Example 2; 120 mg, 0.2 mmol) in THF (1 ml) was treated with triethylamine (60 mg, 0.6 mmol) at room temperature. To this suspension was added ethyl chloroformate (50 mg, 0.4 mmol) at 0° C. After 30 min, NH3 aq (10 ml) was added at 0° C. The solvent was removed. The crude was extracted with $CH_2Cl_2$ three times. The combined extracts were dried over $Na_2SO_4$ and concentrated to give oil, which was purified by a column chromatography on silicagel to give a solid (65 mg, 0.14 mmol, 70%)
$^1$H NMR (CDCl$_3$) δ 7.77 (br, 1H), 7.42 (br, 2H), 7.32–7.06 (m, 10H), 5.30 (br, 2H), 4.39 (d, J=12Hz, 1H), 4.22 (d, J=12Hz, 1H), 3.85–3.60 (m, 3H), 3.33–2.65 (m, 5H), 2.37 (br, 1H), 2.00–1.32 (m, 2H).
Elemental Analysis (0.5 H$_2$O) for $C_{30}H_{28}N_2O_2F_6$:
 Calcd. C: 63.04% H: 5.11% N: 4.90%
 Found C: 62.81% H: 5.27% N: 4.55%

Example 6
(3S,4R,5S,6S)-N,N-(3-Oxa-1,5-pentylene)-6-diphenylmethyl-5-(3,5-bis(trifluoromethyl)benzyoxy)-1-azabicyclo[2.2.2]octane-3-carboxamide To a suspension of (3S,4R,5S,6S)-6-diphenylmethyl-5-(3,5-bis(trifluoromethyl)benzyoxy)-1-azabicyclo[2.2.2]octane-3-carboxylic acid hydrochloride (obtained in Example 2; 120 mg, 0.2 mmol) and morpholine (30 mg, 0.25 mmol) in DMF (1 ml) was added 3-dimethylaminopropyl ethyl carbodiimide (100 mg, 0.5 mmol) at room temperature. The mixture was stirred at room temperature for 18 hr, poured into 2N NaOH aq and extracted with $CH_2Cl_2$ three times. The combined extracts were dried over $Na_2SO_4$ and concentrated to give oil, which was purified by a column chromatography on silicagel to give a solid (100 mg, 0.16 mmol, 79%)
$^1$H NMR (CDCl$_3$) δ 7.79 (br, 1H), 740–7.08 (m, 12H), 4.38 (d, J=12Hz, 1H), 4.13 (d, J=12Hz, 1H), 3.93–2.64 (m, 16H), 2.24 (br, 1H), 2.05–1.23 (m, 2H).
Elemental Analysis (0.5 H$_2$O) for $C_{34}H_{35}N_2O_3F_6$:
 Calcd. C: 63.54% H: 5.65% N: 4.36%
 Found C: 63.70% H: 5.44% N: 4.21%

Example 7
Methyl (3S,4R,5S,6S)-6-Diphenylmethyl-5-(3,5-bis (trifluoromethyl)benzyoxy)-1-azabicyclo[2.2.2]octane-3-carboxylate A solution of (3S,4R,5S,6S)-6-diphenylmethyl-5-(3,5-bis (trifluoromethyl)benzyoxy)-1-azabicyclo[2.2.2]octane-3-carboxylic acid hydrochloride (obtained in Example 2; 120 mg, 0.2 mmol) in HCl—MeOH (5 ml) was heated at reflux temperature for 6 hr, poured into NaHCO3 aq and extracted with $CH_2Cl_2$ three times. The combined extracts were dried over $Na_2SO_4$ and concentrated to give oil, which was purified by a column chromatography on silicagel to give a solid (70 mg, 0.12 mmol, 55%)
$^1$H NMR (CDCl$_3$) δ 7.77 (br, 1H), 7.43 (br, 2H), 7.30–7.16 (m, 10H), 4.38 (d, J=12Hz, 1H), 4.25 (d, J=12Hz, 1H), 3.82–3.60 (m, 3H), 3.70 (s, 3H), 3.30–3.13 (m, 2H), 2.95–2.65 (m, 3H), 2.52 (br, 1H), 1.76–1.35 (m, 2H).
Elemental Analysis for $C_{31}H_{30}N_1O_3F_6$:
 Calcd. C: 64.36% H: 5.23% N: 2.42%
 Found C: 64.40% H: 5.03% N: 2.39%

Example 8
(3S,4R,5S 6S)-6-Diphenylmethyl-5-(3.5-bis (trifluoromethyl)benzyoxy)-3-hydroxymethyl-1-azabicyclo[2.2.2]octane A solution of (3S,4R,5S,6S)-N,N-dimethyl-6-diphenylmethyl-5-(3,5-bis(trifluoromethyl)benzyoxy)-1-azabicyclo[2.2.2]octane-3-carboxamide (obtained in Example 1(v); 100 mg, 0.16 mmol) and LiBHEt$_3$ in THF (2 ml) was stirred at 0° C. for 6 hr, poured into water (10 ml), and extracted with $CH_2Cl_2$ three times. The combined extracts were dried over $Na_2SO_4$ and concentrated to give oil, which was purified by a column chromatography on silicagel to give a solid (60 mg, 0.11 mmol, 69%)
$^1$H NMR (CDCl$_3$) δ 7.75 (br, 1H), 7.41 (br, 2H), 7.38–7.05 (m, 10H), 4.42 (d, J=12Hz, 1H), 4.29 (d, J=12Hz, 1H), 3.88–3.50 (m, 5H), 3.36–3.22 (m, 1H), 2.85–2.60 (m, 2H), 2.36–2.15 (m, 3H), 1.90–1.30 (m, 2H).
Elemental Analysis for $C_{30}H_{29}NO_2F_6$:
 Calcd. C: 65.57% H: 5.32% N: 2.55%
 Found C: 65.54% H: 5.52% N: 2.54%

Example 9
(3S,4R,5S,6S)-6-diphenylmethyl-5-(3-trifluoromethylbenzyoxy)-1-azabicyclo[2.2.2]octane-3-carboxylic acid hydrochloride This compound was prepared in the same manner as in Example 2.
$^1$H-NMR (DMSO-d$_6$) δ 13.13 (br, 1H), 8.14 (br, 1H), 7.68–7.15 (m, 14H), 5.17 (br, 1H), 4.64 (d, J=12Hz, 1H), 4.44 (d, J=12Hz, 1H), 4.04 (br, 1H), 3.76–2.88 (m, 6H), 2.10–1.70 (m, 2H).
Elemental Analysis for $C_{29}H_{29}NO_3F_3$·HCl:
 Calcd. C: 65.47% H: 5.49% N: 2.63%
 Found C: 65.51% H: 5.39% N: 2.72%

Example 10
(3S,4R,5S,6S)-N,N-Dimethyl-6-diphenylmethyl-5-(3-trifluoromethylbenzyoxy)-1-azabicyclo[2.2.2]octane-3-carboxamide The title compound was prepared in the same manner as in Example 1 (v).
$^1$H-NMR (CDCl$_3$) δ7.57–7.02 (m, 14H), 4.43 (d, J=12Hz, 1H), 4.05 (d, J=11Hz, 1H), 3.90–2.62 (m, 8H), 2.93 (s, 3H), 2.88 (s, 3H), 2.24 (br, 1H), 1.92–1.25 (m, 2H).

Example 11
(3S,4R,5S,6S)-6-diphenylmethyl-5-(3-fluoro-5-trifluoromethylbenzyoxy)-1-azabicyclo[2.2.2]octane-3-carboxylic acid hydrochloride This compound was prepared in the same manner as in Example 2.
$^1$H-NMR (DMSO-d$_6$) δ 8.13 (br, 1H), 7.65–7.08 (m, 12H), 5.13 (br, 1H), 4.68 (d, J=12Hz, 1H), 4.48 (d, J=12Hz, 1H), 4.13–2.85 (m, 8H), 2.10–1.71 (m, 2H).
Elemental Analysis (1.5 H$_2$O) for $C_{29}H_{29}NO_3F4$·HCl:
 Calcd. C: 60.26% H: 5.58% N: 2.42%
 Found C: 59.99% H: 5.49% N: 2.22%

Example 12
(3S,4R,5S,6S) N,N-Dimethyl-6-diphenylmethyl-5-(3-fluoro-5-trifluoromethylbenzyoxy)-1-azabicyclo[2.2.2] octane-3-carboxamide The title compound was prepared in the same manner as in Example 1 (v).
$^1$H-NMR (CDCl$_3$) δ 7.36–6.70 (m, 13H), 4.42 (d, J=12Hz, 1H), 4.09 (d, J=12Hz, 1H), 3.90–2.60 (m, 8H), 2.94 (s, 3H), 2.92 (s, 3H), 2.26 (br, 1H), 1.96–1.30 (m, 2H).

Example 13
(3S,4R,5S,6S) 6-diphenylmethyl-5-(3.5-difluorobenzyoxy)-1-azabicyclo[2.2.2]octane-3-carboxylic acid hydrochloride This compound was prepared in the same manner as in Example 2.

$^1$H-NMR (DMSO-d$_6$) δ 8.21–6.65 (m, 13H), 5.09 (br, 1H), 4.75–2.80 (m, 10H), 2.05–1.72 (m, 2H).

Elemental Analysis (0.2 H$_2$O) for C$_{30}$H$_{29}$NO$_3$F$_2$ .HCl:
  Calcd. C: 66.65% H: 5.87% N: 2.78%
  Found. C: 66.67% H: 5.52% N: 2.84%

Example 14
(3S,4R,5S,6S) N,N-Dimethyl-6-diphenylmethyl-5-(3,5-difluorobenzyoxy)-1-azabicyclo[2.2.2]octane-3-carboxamide The title compound was prepared in the same manner as in Example 1 (v).

$^1$H-NMR (CDCl$_3$) δ 7.36–6.40 (m, 13H), 4.43 (d, J=12Hz, 1H), 3.99 (d, J=12Hz, 1H), 3.86–2.62 (m, 8H), 3.68 (s, 6H), 2.23 (br, 1H), 1.92–1.25 (m, 2H).

Example 15
(3S,4R,5S,6S)-N,N-Diethyl-6-diphenylmethyl-5-(3,5-bis(trifluoromethyl)benzyoxy)-1-azabicyclo[2.2.2]octane-3-carboxamide To a suspension of (3R,4R,5S,6S)-N,N-Diethyl-6-diphenylmethyl-5-hydroxy-1-azabicyclo[2.2.2]octane-3-carboxamide (obtained in Example 25 below; 120 mg, 0.25 mmol) in DME (3 ml) was added potassium t-butoxide (40 mg, 0.3 mmol) followed by 18-crown-6 (70 mg, 0.3 mmol) at 0° C. To this solution was added 3,5-bis(trifluoromethyl) benzyl bromide (90 mg, 0.3 mmol) in DME (1 ml) at 0° C. The mixture was stirred at 0° C. for 1 hr, quenched with H$_2$O (10 ml), and extracted with CH$_2$Cl$_2$ three times. The combined extracts were dried over Na$_2$SO$_4$ and concentrated. The crude was purified by recrystallization from MeOH (1 ml) to give a title compound (53 mg, 0.09 mmol, 36%)

$^1$H NMR (CDCl$_3$) δ 7.79 (br, 1H), 7.37 (br, 2H), 7.37–7.08 (m, 10H), 4.40 (d, J=12Hz, 1H), 4.21 (d, J=12Hz, 1H), 3.95–3.08 (m, 11H), 2.76–1.20 (m, 4H), 1.18–1.00 (m, 6H).

Elemental Analysis for C$_{34}$H$_{36}$N$_2$O$_2$F$_6$:
  Calcd. C: 66.01% H: 5.87% N: 4.53%
  Found C: 65.79% H: 5.83% N: 4.48%

Example 16
(3R,4S,5S,6S)-N,N-Dimethyl-6-diphenylmethyl-5-(3,5-bis(trifluoromethylbenzyoxy)-1-azabicyclo[2.2.2]octane-3-carboxamide To a suspension of (3R,4S,5S,6S)-N,N-Dimethyl-6-diphenylmethyl-5-hydroxy-1-azabicyclo[2.2.2]octane-3-carboxamide (obtained in Example 26 below; 90 mg, 0.25 mmol) in DME (3 ml) was added potassium t-butoxide (60 mg, 0.5 mmol) followed by 18-crown-6 (140 mg, 0.5 mmol) at 0° C. To this solution was added 3,5-bis(trifluoromethyl) benzyl bromide (160 mg, 0.5 mmol) in DME (1 ml) at 0° C. The mixture was stirred at 0° C. for 1 hr, quenched with H$_2$O (20 ml), and extracted with CH$_2$Cl$_2$ three times. The combined extracts were dried over Na$_2$SO$_4$ and concentrated. The crude was purified by acolumn chromatography to give a title compound (120 mg, 0.2 mmol, 80%)

$^1$H NMR (CDCl$_3$) δ 7.78 (br, 1H), 7.43 (br, 2H), 7.32–7.00 (m, 10H), 4.45 (d, J=11Hz, 1H), 4.29 (d, J=11Hz, 1H), 3.80–2.68 (m, 8H), 3.02 (s, 3H), 2.97 (s, 3H), 2.37(br, 1H), 2.00–1.50 (m, 2H).

Example 17
(3R,4S,5S,6S)-6-diphenylmethyl-5-(3,5-bis(trifluoromethyl)benzyoxy)-1-azabicyclo[2.2.2]octane-3-carboxylic acid hydrochloride A solution of (3R,4S,5S,6S)-N,N-Dimethyl-6-diphenylmethyl-5-(3,5-bis(trifluoromethyl)benzyoxy)-1-azabicyclo[2.2.2]octane-3-carboxamide (obtained in Example 16; 100 mg, 0.16 mmol) in conc. HCl (1 ml) was heated at reflux for 2.5 hr. The resulting precipitate was collected and dried to give a title compound (60 mg, 0.12 mmol, 70%).

$^1$H-NMR (CDCl$_3$) δ 8.23–7.12 (m, 13H), 5.11 (br, 1H), 4.68 (d, J=12Hz, 1H), 4.58 (d, J=12Hz, 1H), 4.13 (br, 1H), 3.70–2.90 (m, 7H), 2.06–1.61 (m, 2H).

Elemental Analysis (H$_2$O) for C$_{30}$H$_{27}$NO$_3$F$_6$.HCl:
  Calcd. C: 58.21% H: 5.05% N: 2.26%
  Found C: 58.24% H: 4.65% N: 2.46%

Example 18
3,5-Dimethylbenzyl (3S,4R,5S,6S)-6-Diphenylmethyl-5-(3,5-dimethylbenzyoxy-1-azabicyclo[2.2.2]octane-3-carboxylate To a suspension of (3S,4R,5S,6S) 6-diphenylmethyl-5-hydroxy-1-azabicyclo[2.2.2]octane-3-carboxylic acid hydrochloride (obtained in Example 1 (iii); 380 mg, 1 mmol) in DME (15 ml) was added potassium t-butoxide (450 mg, 4 mmol) followed by 18-crown-6 (1.0 g, 4 mmol) at room temp. To this solution was added 3,5-dimethylbenzyl bromide (800 mg, 4 mmol) in DME (3 ml) at 0° C. The mixture was stirred at 0° C. for 1 hr and at room temp for 15 hr, quenched with H$_2$O (10 ml), and extracted with CH$_2$Cl$_2$ three times. The combined extracts were dried over Na$_2$SO$_4$ and concentrated. The crude was purified by a column chromatography on silicagel to give a title compound (180 mg, 0.29 mmol, 29%)

$^1$H-NMR (CDCl$_3$) δ 7.38–6.52 (m, 16H), 5.01 (s, 2H), 4.65 (d, J=12Hz, 1H), 4.43 (d, J=12Hz, 1H), 3.75–3.68 (m, 3H), 3.30–2.62 (m, 5H), 2.30 (s, 3H), 2.24 (s, 3H), 2.54 (br, 1H), 1.71–1.26 (m, 2H).

Example 19
(3S,4R,5S,6S)-6-Diphenylmethyl-5-(3,5-dimethylbenzyoxy)-1-azabicyclo[2.2.2]octane-3-carboxylic acid A mixture comprising 3,5-Dimethylbenzyl (3S,4R,5S,6S)-6-Diphenylmethyl-5-(3,5-dimethylbenzyoxy)-1-azabicyclo[2.2.2]octane-3-carboxylate (obtained in Example 18; 180 mg, 0.29 mmol) and Pd—C (50 mg) in MeOH (10 ml) was stirred at room temp. for 15 hr. The resulting precipitate was collected and dried to give a title compound (70 mg, 0.14 mmol, 48%).

$^1$H-NMR (CDCl$_3$) δ 7.37–7.05 (m, 10H), 6.87 (br, 1H), 6.48 (br, 2H), 4.46 (d, J=12Hz, 1H), 4.17 (d, J=12Hz, 1H), 4.04–3.65 (m, 2H), 3.64 (d, J=12Hz, 1H), 3.40–2.62 (m, 6H), 2.25 (s, 6H), 1.96–1.35 (m, 2H).

Elemental Analysis (2.7 H$_2$O) for C$_{32}$H$_{33}$NO$_3$:
  Calcd. C: 71.46% H: 7.68% N: 2.78%
  Found C: 71.24% H: 7.54% N: 2.73%

Example 20
(3S,4R,5S,6S)-6-Diphenylmethyl-5-(5-isopropyl-2-methoxybenzyoxy)-1-azabicyclo[2.2.2]octane-3-carboxylic acid hydrochloride This compound was prepared in the same manner as in Example 18. This compound was isolated as hydrochloride salt.

$^1$H-NMR (CDCl$_3$, free base) δ 7.60–6.67 (m, 13H), 4.74 (br, 1H), 4.50–2.80 (m, 12H), 3.79 (s, 3H), 2.10–0.82 (m, 8H).

Elementa Analysis (1.5 H$_2$O) for C$_{32}$H$_{38}$NO$_4$.HCl:
  Calcd. C: 68.25% H: 7.34% N: 2.49%
  Found C: 65.51% H: 5.39% N: 2.72%

Example 21
5-isopropyl-2-methoxybenzyl (3S,4R,5S,6S) 6-diphenylmethyl-5-(5-isopropyl-2-methoxybenzyoxy)-1-azabicyclo[2.2.2]octane-3-carboxylate The title compound was prepared in the same manner as in Example 19.
H-NMR (CDCl$_3$) δ 7.46–6.62 (m, 16H), 5.21 (d, J=12Hz, 1H), 5.11 (d, J=12Hz, 1H), 4.50–4.18 (m, 2H), 3.88–2.54 (m, 11H), 3.77 (s, 3H), 3.59 (s, 3H), 1.80–1.12 (m, 14H).

Example 22
5-isopropyl-2-methoxybenzyl (3S,4R,5S,6S)-6-diphenylmethyl-5-hydroxy-1-azabicyclo[2.2.2]octane-3-carboxylate To a suspension of (3S,4R,5S,6S)-6-diphenylmethyl-5-hydroxy-1-azabicyclo[2.2.2]octane-3-carboxylic acid hydrochloride (obtained in Example 1 (iii); 110 mg, 0.3 mmol) in DME (3 ml) was added potassium t-butoxide (130 mg, 1.2 mmol) followed by 18-crown-6 (300 mg, 1.2 mmol) at room temperature. To this solution was added 5-isopropyl-2-methoxybenzyl bromide (300 mg, 1.2 mmol) in DME (3 ml) at 0° C. The mixture was stirred at 0° C. for 1 hour and at room temperature for 1 hour, quenched with H$_2$O (10 ml), and extracted with CH$_2$Cl$_2$ three times. The combined extracts were dried over Na$_2$SO$_4$ and concentrated. The crude was purified by a column chromatography on silicagel to give a title compound (120 mg, 0.23 mmol, 78%).
$^1$H-NMR (CDCl$_3$) δ 7.48–6.78 (m, 13H), 5.24 (d, J=12Hz, 1H), 5.13 (d, J=12Hz, 1H), 4.42 (d, J=12Hz, 1H1), 4.09–4.00 (m, 1H), 3.78 (s, 3H), 3.70–3.58 (m, 1H), 3.35–2.63 (m, 6H), 2.40 (br, 1H), 1.80–1.20 (m, 3H).

Example 23
3,5-Dimethylbenzyl (3S,4R,5S,6S)-6-Diphenylmethyl-5-hydroxy-1-azabicyclo[2.2.2]octane-3-carboxylate The title compound was prepared in the same manner as in Example 22.
$^1$H-NMR (CDCl$_3$) δ 7.48–6.90 (m, 13H), 5.12–5.01 (m, 2H), 4.40 (d, J=12Hz, 1H), 4.10–4.00 (m, 1H), 3.70–3.58 (m, 1H), 3.34–3.07 (m, 3H), 3.00 (s, 3H), 3.00 (s, 3H), 2.93–2.64 (m, 2H), 2.40 (br, 1H), 1.74–1.30 (m, 3H).

Example 24
Methyl (3S,4R,5S,6S)-6-diphenylmethyl-5-hydroxy-1-azabicyclo[2.2.2]octane-3-carboxylate The title compound was prepared in the same manner as in Example 7.
$^1$H-NMR (CDCl$_3$) δ 7.48–7.07 (m, 10H), 4.41 (d, J=12Hz, 1H), 4.10–4.03 (m, 1H), 3.71–3.60 (m, 1H), 3.69 (s, 3H), 3.34–3.04 (m, 3H), 2.93–2.65 (m, 2H), 2.36 (br, 1H), 1.73–1.34 (m, 3H).

Example 25
(3R,4R,5S,6S)-N,N-Diethyl-6-diphelmethyl-5-hydroxy-1-azabicyclo[2,2,2]octane-3-carboxamide The title compound was prepared in the same manner as in Example 1(ii).
$^1$H-NMR (CDCl$_3$) δ 7.50–7.08 (m, 10H), 6.27 (d, J=6Hz, 1H), 4.61 (d, J=12Hz, 1H), 3.92–2.30 (m, 12H), 1.73–1.10 (m, 8H).

Example 26
(3R,4S,5S,6S)-N,N-Dimethyl-6-diphenylmethyl-5-hydroxy-1-azabicyclo[2.2.2]octane-3-carboxamide The title compound was prepared in the same manner as in Example 1(ii).
$^1$H-NMR (CDCl$_3$) δ 7.50–7.10 (m, 10H), 4.49 (d, J=12Hz, 1H), 4.08–4.00 (m, 1H), 3.68–2.69 (m, 2H), 3.02 (s, 3H), 2.96 (s, 3H), 2.14 (br, 1H), 1.85–1.43 (m, 3H).

We claim:

1. A compound of general formula (I) and a pharmaceutically acceptable salt thereof:

wherein

X and Y are each independently hydrogen, halo, $C_1$–$C_6$ alkyl, halosubstituted $C_1$–$C_6$ alkyl, $C_1$–$C_6$ alkoxy, $C_1$–$C_6$ alkylthio, $C_1$–$C_6$ alkylsulfinyl, $C_1$–C6 alkylsulfonyl or tri($C_1$–$C_6$ alkyl)silyl;

Ar$^1$ and Ar$^2$ are each independently selected from the group consisting of phenyl, naphthyl, pyridyl, quinolyl, thienyl, furyl, oxazolyl, tetrazolyl, thiazolyl, imidazolyl, and pyrazolyl, optionally substituted by halo;

Z-A- has a point of attachment at the 2- or 3-position of the quinuclidine ring;

A is —CO— when Z is -NR$^1$R$^2$ or W$^1$-(CH$_2$)$_m$-CHR$^4$-(CH$_2$)$_n$-NR$^3$-, or -(CH$_2$)- when Z is hydroxy, $C_1$–$C_6$ alkoxy, NR$^1$R$^2$ or W$^1$-(CH$_2$)$_m$-CHR$^4$-(CH$_2$)$_n$-NR$^3$-;

wherein

R$^1$ and R$^2$ when taken separately are each independently hydrogen or $C_1$–$C_6$ alkyl;

R$^1$ and R$^2$ when taken together with the nitrogen atom to which they are attached represent piperidino, pyrrolidino, morpholino, thiomorpholino or piperazino;

R$^3$ is hydrogen, $C_1$–$C_6$ alkyl, benzyl or -(CH$_2$)$_r$-W$^2$;

R$^4$ is hydrogen or $C_1$–$C_6$ alkyl which may be substituted by hydroxy, amino, methylthio, mercapto, benzyl, 4-hydroxybenzyl, 3-indolylmethyl or -(CH$_2$)$_s$-W$^3$;

R$^3$ and R$^4$ when taken together represent CH$_2$ or CH$_2$CH$_2$;

W$^1$, W$^2$ and W$^3$ are each independently cyano, hydroxymethyl, $C_2$–$C_6$ alkoxymethyl, aminomethyl, mono($C_1$–$C_6$ alkylamino)methyl or di($C_1$–$C_6$ alkylamino)methyl, carboxyl, mono($C_1$–$C_6$ alkyl)carbamoyl or di($C_1$–$C_6$ alkyl)carbamoyl, carbamoyl or ($C_1$–$C_6$alkoxy)carbonyl; and m, n, r and s are each 0, 1, 2 or 3.

2. A compound according to claim 1 wherein Ar$^1$ and Ar$^2$ are each phenyl.

3. A compound according to claim 2, wherein Z-A- is at the 3-position; and A is —CO—.

4. A compound according to claim 3 wherein Z is -NR$^1$R$^2$ wherein R$^1$ and R$^2$ are each —H, —CH$_3$ or —CH$_2$CH$_3$.

5. A compound according to claim 4, wherein X is hydrogen, 3-CH$_3$, 3-CF$_3$ or 3-F; and Y is 5-CH$_3$, 5-CF$_3$ or 5-F.

6. A compound according to claim 5, wherein Z is —NH$_2$; X is hydrogen, 3-CF$_3$, 3-CH$_3$ or 3-F; and Y is 5-CF$_3$, 5-CH$_3$ or 5-F.

7. A compound according to claim 3, wherein Z is NH$_2$COCH$_2$NH—; X is hydrogen, 3-CF$_3$, 3-CH$_3$ or 3-F; and Y is 5-CF$_3$, 5-CH$_3$ or 5-F.

8. A compound according to claim 2, wherein Z-A- is at the 3-position; A is -(CH₂)-; Z is OH; X is hydrogen, 3-CF₃, 3-CH₃ or 3-F; and Y is 5-CF₃, 5-CH₃ or 5-F.

9. A compound according to any one of claims 1 to 5 and 6 to 8, wherein the stereochemistry is 3S,4R,5S,6S or 3R,4S,5S,6S.

10. A compound according to claim 1, being one of the following:

(3S,4R,5S,6S)-N-Carbamoylmethyl-6-diphenylmethyl-5-(3,5-bis(trifluoromethyl)benzyloxy)-1-azabicyclo[2.2.2]octane-3-carboxamide;

(3S,4R,5S,6S)-6-Diphenylmethyl-5-(3,5-bis(trifluoromethyl)benzyloxy)-1-azabicyclo[2.2.2]octane-3-carboxamide;

(3S,4R,5S,6S)-N,N-(3-Oxa-1,5-pentylene)-6-diphenylmethyl-5-(3,5-bis(trifluoromethyl)benzyloxy)-1-azabicyclo[2.2.2]octane-3-carboxamide;

(3S,4R,5S,6S)-N,N-Diethyl-6-diphenylmethyl-5-(3,5-bis(trifluoromethyl)benzyloxy)-1-azabicyclo[2.2.2]octane-3-carboxamide; and (3S,4R,5S,6S)-N,N-Dimethyl-6-diphenylmethyl-5-(3,5-bis(trifluoromethyl)benzyloxy)-1-azabicyclo[2.2.2]octane-3-carboxamide.

11. A method of treating an inflammatory disease in a mammalian subject which comprises administering to said subject a therapeutically effective amount of a compound of claim 1.

12. A compound of the formula:

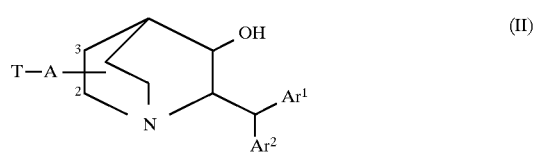

wherein

Ar¹ and Ar² are each independently selected from the group consisting of phenyl, naphthyl, pyridyl, quinolyl, thienyl, furyl, oxazolyl, tetrazolyl, thiazolyl, imidazolyl, and pyrazolyl, optionally substituted by halogen;

A is —CO— or -(CH₂)-;

T-A- has a point of attachment at the 2- or 3-position on the quinuclidine ring;

T is NR¹R² or benzyloxy optionally substituted with one or two substituents selected from the group consisting of C₁–C6 alkyl, C₁–C₆alkoxy and halosubstituted C₁–C₆ alkyl;

R¹ and R² when taken separately are each independently hydrogen or C₁–C₆ alkyl; and R¹ and R² when taken together with the nitrogen atom to which they are attached represent piperidino, pyrrolidino, morpholino, thiomorpholino or piperazino.

13. A compound according to 12, wherein A is —CO—; and T is NR¹R².

14. A compound according to claim 12, wherein A is —CO—; and T is benzyloxy optionally substituted with one or two substituents selected from C₁–C₆ alkyl and C₁–C₆ alkoxy.

15. A compound according to claim 13 or 14, wherein the stereochemistry is 3S,4R,5S,6S.

16. A compound of general formula (I-b) and a pharmaceutically acceptable salt thereof:

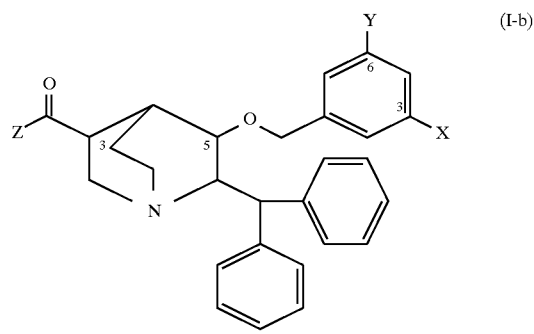

wherein

X is H, CF₃, CH₃, or F;

Y is CF₃, CH₃, or F; and

Z is NH₂COCH₂NH—.

17. A method of treating in a mammalian subject, a condition at least partially mediated by substance P, associated with an excess of substance P activity, and responding favorably to significant antagonism of substance P receptors, wherein said condition is an inflammatory disease, comprising administering to said subject an amount therapeutically effective to treat said inflammatory disease, of a compound of the formula:

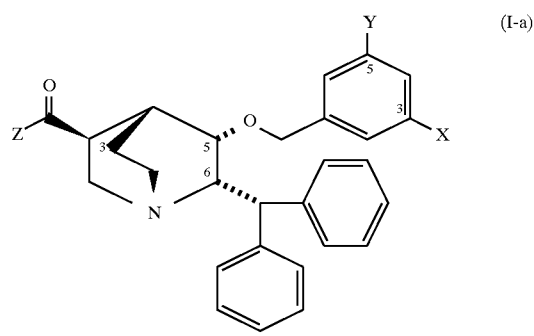

wherein

X is independently selected from the group consisting of —H, —F, —CH₃, and —CF₃;

Y is independently selected from the group consisting of —F, —CH₃, and —CF₃;

Z is independently selected from the group consisting of —NR¹R² where R¹ and R² are each independently —H, —CH₃, or —CH₂CH₃; and pharmaceutically acceptable salt forms thereof.

18. A pharmaceutical composition for treating in a mammalian subject, a condition at least partially mediated by substance P, associated with an excess of substance P activity, and responding favorably to significant antagonism of substance P receptors, wherein said condition is an inflammatory disease, comprising:

(A) an amount therapeutically effective to treat said inflammatory disease, of a compound of the formula:

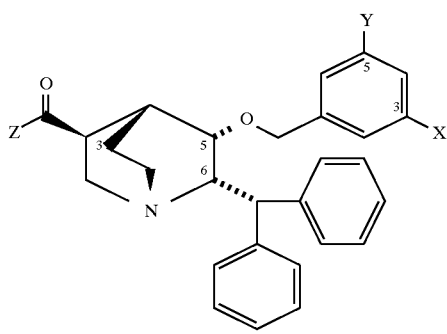

(I-a)

wherein

X is independently selected from the group consisting of —H, —F, —CH$_3$, and —CF$_3$;

Y is independently selected from the group consisting of —F, —CH$_3$, and —CF$_3$;

Z is independently selected from the group consisting of —NR$^1$R$^2$ where R$^1$ and R$^2$ are each independently —H, —CH$_3$, or —CH$_2$CH$_3$; and pharmaceutically acceptable salt forms thereof; together with (B) a pharmaceutically acceptable carrier therefor.

* * * * *